(12) United States Patent
Hoerstrup et al.

(10) Patent No.: US 8,636,793 B2
(45) Date of Patent: Jan. 28, 2014

(54) TUBULAR SUPPORTING PROSTHESIS CAPABLE OF GROWING

(75) Inventors: Simon-Philipp Hoerstrup, Zurich (CH); Gregor Zund, Herrliberg (CH); Thilo Fliedner, Munich (DE); Frank Baaijens, Eindhoven (NL)

(73) Assignee: Universität Zürich, Zurich (CH)

( * ) Notice: Subject to any disclaimer, the term of this patent is extended or adjusted under 35 U.S.C. 154(b) by 0 days.

(21) Appl. No.: 12/527,132

(22) PCT Filed: Feb. 15, 2008

(86) PCT No.: PCT/EP2008/001172
§ 371 (c)(1),
(2), (4) Date: May 25, 2010

(87) PCT Pub. No.: WO2008/098776
PCT Pub. Date: Aug. 21, 2008

(65) Prior Publication Data
US 2011/0060401 A1    Mar. 10, 2011

(30) Foreign Application Priority Data
Feb. 16, 2007 (EP) .................................. 07003351

(51) Int. Cl.
*A61F 2/24* (2006.01)
*A61F 2/06* (2013.01)

(52) U.S. Cl.
USPC .......... 623/1.2; 623/1.26; 623/1.46; 623/2.14; 623/2.18

(58) Field of Classification Search
USPC ................................................. 623/1.2, 1.26
See application file for complete search history.

(56) References Cited

U.S. PATENT DOCUMENTS

2003/0105513 A1* 6/2003 Moriuchi et al. ............ 623/1.15
2004/0260389 A1* 12/2004 Case et al. .................. 623/1.24
2006/0122694 A1* 6/2006 Stinson et al. ............... 623/1.34

OTHER PUBLICATIONS

Breuer CK, Shin'oka T, Tanel RE, Zund G, Mooney DJ, Ma PX, Miura T, Colan S, Langer R, Mayer JE, Vacanti JP. Tissue engineering lamb heart valve leaflets. Biotechnol Bioeng. Jun. 5, 1996;50(5):562-7. Publ. Date: May 6, 1996.

Hill, Ronald J. et al., Quantitation of Types I and III Collagens in Human Tissue Samples and Cell Culture by Cyanogen Bromide Peptide Analysis, Analytical Biochemistry 141, 83-93 (1984).

Hoerstrup et al, Functional living Trileaflet, Functional Living Trileaflet Heart Valves Grown In Vitro Circulation 2000; 102;44-49; Publ. date Jul. 11, 2000.

Hoerstrup SP, Sodian R, Sperling JS, Vacanti JP, Mayer JE Jr. New pulsatile bioreactor for in vitro formation of tissue engineered heart valves. Tissue Eng. Feb. 2000;6(1):75-9. Publ. Date: Jun. 2000.

(Continued)

*Primary Examiner* — Bruce E Snow
*Assistant Examiner* — Brian Dukert
(74) *Attorney, Agent, or Firm* — Sughrue Mion, PLLC (57) ABSTRACT

The invention relates to a tubular supporting prosthesis capable of growing, comprising a mesh structure, wherein the mesh structure comprises at least two structural rings, which are connected to each other via connecting members and are disposed point-symmetrically about the longitudinal supporting prosthesis axis, wherein the structural rings and/or the connecting members have at least one predetermined breaking point.

31 Claims, 4 Drawing Sheets

(56) References Cited

OTHER PUBLICATIONS

Hoerstrup SP, Zund G, YE Q, Schoeberlein A, Schmid AC, Turina MI. Tissue engineering of a bioprosthetic heart valve: stimulation of extracellular matrix assessed by hydroxyproline assay. ASAIO J. Sep.-Oct. 1999;45(5):397-402. Publ. Date: Oct. 1999.

Hoerstrup, Simon P., et al, Functional Grown in Tissue-Engineered Living, Vascular Grafts: Follow-Up at 100 Weeks in a Large Animal Model, Journal of American Heart Association; Circulations 2006; 114; 159-166.

Kanda K, Matsuda T. Behavior of arterial wall cells cultured on periodically stretched substrates. Cell Transplant. Nov.-Dec. 1993; 2 (6):475-84. Publ. Date: Nov. or Dec. 1993.

Mooney DJ, Breuer C, McNamara K, Vacanti JP, Langer R. Fabricating tubular devices from polymers of lactic and glycolic Acid for tissue engineering. Tissue Eng. 1995 Summer;1(2):107-18. Publ. Date: Feb. 1995.

Mooney DJ, Organ G, Vacanti JP, Langer R. Design and fabrication of biodegradable polymer devices to engineer tubular tissues. Cell Transplant. Mar.-Apr. 1994 ;3(2):203-10.Publ. Date: Mar. or Apr. 1994 (?).

Shinoka T, Breuer CK, Tanel RE, Zund G, Miura T, Ma PX, Langer R, Vacanti JP, Mayer JE Jr. Tissue engineering heart valves: valve leaflet replacement study in a lamb model. Ann Thorac Surg. Dec. 1995;60(6 Suppl):S513-6. Publ. Date: Presentation Apr. 20-22, 1995 in Boston.

Shinoka T, Ma PX, Shum-Tim D, Breuer CK, Cusick RA, Zund G, Langer R, Vacanti JP, Mayer JE Jr. Tissue-engineered heart valves. Autologous valve leaflet replacement study in a lamb model. Circulation. Nov. 1, 1996;94(9 Suppl):II164-8 Publ. Date: Jan. 11, 1996.

Sodian, et al, Early in vivo experience with Tissue-Engineered Trileaflet Heart Valves, Circulation 2000; 102, 22-29; Publ. date Jul. 11, 2000.

Zünd et al; The in vitro construction of a tissue engineered bioprosthetic heart valve, European Journal of Cardio-Thoracic Surgery, 1997; 11:493-497; Publ. Date: Presented Sep. 24-27, 1995 in Paris.

Zünd G, Hoerstrup SP, Schoeberlein A, Lachat M, Uhlschmid G, Vogt PR, Turina M. Tissue engineering: a new approach in cardiovascular surgery: Seeding of human fibroblasts followed by human endothelial cells on resorbable mesh. Eur J Cardiothorac Surg. Feb. 1998;13(2):160-4. Publ. Date: Presented 28.9-1.10.1997.

* cited by examiner

TUBULAR SUPPORTING PROSTHESIS CAPABLE OF GROWING

CROSS REFERENCE TO RELATED APPLICATIONS

This application is a National Stage of International Application No. PCT/EP2008/001172, filed on Feb. 15, 2008, claiming priority based on European Patent Application EP 07003351.9, filed on Feb. 16, 2007, the contents of all of which are incorporated herein by reference in their entirety.

FIELD OF THE INVENTION

The present invention describes a tubular supporting prosthesis for supporting a blood vessel or heart valve.

BACKGROUND OF THE INVENTION

The present invention relates to supporting prostheses which are capable of growth. In particular, the present invention relates to supporting prostheses for supporting a vessel from inside as well as heart valve-carrying or blood vessel-carrying supporting prostheses which can include "tissue engineered" autologous or heterologous tissue or heart valve tissue which is foreign to the body, but which is decellularized or fixed. Such support prostheses can also be called "stents".

Stents are widely used for supporting narrowed or damaged vessels, for example, following cardiological interventional procedures or following invasive surgical procedures. Since their introduction at the end of the seventies, stents have also been very widely used in congenital heart defects.

In treating children, for example newborns with congenital heart diseases, the size of the stents used is adapted to the size of the child's vessel. Thus, a stent implanted in the childhood years must, due to the later growth of the child, either be repeatedly stretched open by means of balloon angioplasty or must be replaced with larger stents in one or more surgical procedures in order to prevent a narrowing.

The prior art has confronted this problem in different manners. There exist stents which are composed of materials which are degradable in the body. Such biologically degradable or bio-absorbable stents can develop their support function shortly following implantation into a vessel and gradually disappear thereafter. Known degradable materials for this purpose are polymers or metals. Such bio-degradable stents are for example described in Erne et al. (2006), Cardiovasc. Intervent. Radiol. 29, 11-16.

However, biologically degradable stents imply certain disadvantages. For one, the disappearance of the stent structure also implies a loss of the support function associated therewith. This loss is a particularly severe problem especially in congenital vessel anomalies since, for one, the desired support function is insufficient and/or is only present for a short period of time, although in most cases it is needed for a long time. Moreover, inflammatory and/or foreign body reactions, in some cases severe, are observed at the vessel wall, primarily due to the dissolution of stents made of biologically degradable polymers.

SUMMARY OF THE INVENTION

The aim of the present invention is thus to provide a supporting prosthesis which can develop the desired support function over longer durations of time, also in the growing organism, wherein the disadvantages mentioned above should be avoided to the greatest possible extent.

According to the invention, this problem is solved by a tubular supporting prosthesis which is capable of growth and which, in some cases, can carry a heart valve, said tubular support prosthesis comprising a mesh structure, wherein the mesh structure comprises at least two structural rings which are connected to each other via connecting members and are disposed point-symmetrically about the longitudinal axis of the supporting prosthesis, wherein the structural rings and/or the connecting members comprise at least one predetermined breaking point.

The inventors have surprisingly found that providing at least one predetermined breaking point in the structural ring and/or in the connecting member of the supporting prosthesis enables a long-term growth of this supporting prosthesis without a significant reduction in the supporting function. In the event that the vessel to be supported or the heart valve region to be supported, for example, in a small child, increases in size with time, the supporting prosthesis according to the invention can grow with it, since the predetermined breaking points can be actively or passively broken. In the event that the supporting prosthesis capable of growth according to the invention additionally comprises a heart valve, for example, a tissue engineered ("TE") heart valve, this has the additional advantage that the heart valve can grow in an analogous manner as the supporting prosthesis. Prior to implantation in a patient, the supporting prosthesis according to the invention can be populated with homologous, preferably with autologous cells, preferably endothelial cells, fibroblasts and/or myofibroblasts and/or further pluripotent progenitor cells and/or stem cells or may be supplemented with tissue which has already been produced in vitro. After a few weeks, these cells form a uniform tissue, including an "integrated" supporting prosthesis, with the vessel wall of the vessel to be supported.

With increasing vessel lumen, forces act on the supporting prosthesis which can lead to point-wise breaks at the predetermined breaking points of the mesh structure of the supporting prosthesis, i.e. the mesh structure of the supporting prosthesis can be broken apart at its predetermined breaking points by the radial forces arising due to growth. In this way, the supporting prosthesis according to the invention (and, as the case may be, also a heart valve contained therein) can automatically adapt to a vessel lumen circumference which has become larger, wherein an adequate support function in ensured by the interaction of the cell tissue populating the supporting prosthesis as well with the fragments of the mesh structure still remaining.

BRIEF DESCRIPTION OF THE DRAWINGS

The following figures and examples describe but do not limit the invention.

The figures show:

FIG. 1A plan view of a segment of the mesh structure of a supporting prosthesis capable of growth according to an embodiment of the invention. The following are shown: A first periodically deformed structural ring (101) and a second periodically deformed structural ring (102), each with crests (103) and troughs (104) which define in their middle the circumferential middle line M. The first and second structural ring (101 and 102) are connected with one another via connecting members (105) fashioned as struts. Predetermined breaking points are shown as black dots which in the embodiment shown are disposed on or next to the middle line M (predetermined breaking points 106), on a crest (predetermined breaking point 107) as well as in a connecting member (predetermined breaking point 108).

DETAILED DESCRIPTION OF THE INVENTION

The term "predetermined breaking point" is generally to be understood such that it is not only in this position in the structural ring and/or connecting member it is not only possible to break or a force open or break apart the predetermined breaking point, but also to stretch the predetermined breaking point. Stretching of the predetermined breaking point is to be viewed as a plastic deformation of this, in which the geometry of the predetermined breaking point changes without necessarily requiring that the parts neighboring the predetermined breaking point are separated. The stretching of a predetermined breaking point can also occur at a preliminary stage of the final breaking of the predetermined breaking point. As such, the interpretations of a predetermined breaking point on the one hand as a breaking point, and on the other hand as a stretching point, do necessarily mutually exclude one another. Although predetermined breaking points will be primarily spoken of in the sense of breaking points in the following text, it is thus clear to the skilled person that, under certain circumstances, a stretching point is (also) to be understood as falling thereunder.

It is possible to design the predetermined breaking points such that these dissolve with time, in order to enable a forcing apart or a breaking apart at the thus generated weak points due to the growth process (passive breaking). An active forcing open of the predetermined breaking points is also conceivable, for example by means of balloon angioplasty, in order to adapt an already implanted supporting prosthesis to a lumen which has increased in size since implantation.

The predetermined breaking points can also be fashioned such that they can be forced open or at least weakened by external influence, for example by the influence of sound waves such as for example ultrasound or shock waves, x-rays, magnetic energy, etc. Design of the predetermined breaking points in this way has the particular advantage that the forcing open of a supporting prosthesis which for example has already been implanted in early childhood years, can later be effected or at least promoted from outside, without the child who has grown in the meantime needing to undergo another operation.

Independently of whether the supporting prosthesis is actively or passively forced open, the predetermined breaking points of the supporting prosthesis according to invention enable the size, e.g. the diameter, of the supporting prosthesis according to the invention to be adapted to the size of the vessel.

According to one embodiment of the present invention, at least one structural ring of the mesh structure comprises n periodic deformations extending longitudinally along the axis of the supporting prosthesis, said deformations forming crests and troughs, said deformations comprising an amplitude A with reference to the longitudinal axis of the supporting prosthesis, wherein n=16-70, preferred 20-56, especially preferred 24-42. Here, A is to be understood as the maximal deviation of a respective deformation from its middle position, that is, from a circumferential middle line M defined for every structural ring (wherein the plane formed by M perpendicularly intersects the longitudinal axis of the supporting prosthesis), A being 0.25-8 mm, preferred 0.75-4 mm, especially preferred 1-2 mm. These deformations, which can be sinusoidal, rectangular, saw-tooth, triangular or meandering in shape, preferably sinusoidal, confer on the supporting prosthesis its foldability and elasticity necessary for insertion by means of a catheter, i.e. they allow the diameter of the supporting prosthesis to be reduced to the required diameter prior to insertion into a patient without substantially shortening the supporting prosthesis in its total length.

In a preferred embodiment, the mesh structure comprises 2 to 8, preferred 2-6, especially preferred 2-4 structural rings.

According to a further embodiment of the present invention, the number of periodic deformations of two respectively neighboring structural rings is identical, or the number of the deformations of two respectively neighboring structural rings differs from one another by a multiple whole number. If the number of the deformations of two respectively neighboring structural rings is identical, every deformation of a structural ring can be connected with every or, for example, every second, third or fourth corresponding deformation of a respectively neighboring structural ring via the connecting members, in order to form the mesh structure. This has the advantage of generating a supporting prosthesis with a very regular mesh structure, which can support the inner wall of a vessel with equivalent force at every point along the total length of the supporting prosthesis. If the number of the deformations of two respectively neighboring structural rings differs from one another by multiple whole number, every deformation of one structural ring can be connected with every second, every third, every fourth etc., deformation of a respectively neighboring structural ring via connecting members. In this way, the density of the mesh structure can be designed differently over the entire length of the supporting prosthesis in order to fulfil different clinical requirements in which differing supporting forces are required along a supported segment of a vessel.

According to this embodiment of the invention, the supporting prosthesis can be designed such that, by suitable selection of the number of deformations of two respectively neighboring structural rings, the radial supporting force of the supporting prosthesis continually decreases or increases from one end to the other end. According to this embodiment of the invention, designs are also conceivable in which the radial supporting force of a prosthesis along the longitudinal axis of the supporting prosthesis decreases toward the middle of the supporting prosthesis i.e. in which this supporting force at each of both ends of the supporting prosthesis is larger than in the middle. Conversely, other designs are possible in which the density of the mesh structure is chosen by suitable choice of the periods of the deformations of two respectively neighboring structural rings, such that the supporting force along the longitudinal axis of the supporting prosthesis is largest in the middle of the supporting prosthesis.

According to a further embodiment of the present invention, two neighboring structural rings can be disposed in a phased-shifted manner with respect to one another, such that crests of one structural ring are connected with troughs of a respectively neighboring structural ring via the connecting elements. In many vessel-supporting prostheses known in the prior art, two neighboring, periodically deformed rings of the prosthesis structure are connected via their respective troughs or crests, that is the crest of one structural ring is connected with the crest of a respectively neighboring structural ring or the trough of one structural ring is connected with the trough of a respectively neighboring ring. If however two neighboring structural rings are point-symmetrically rotated against one another about the longitudinal axis of the supporting prosthesis, so that the crest of one deformed structural ring is disposed opposite the trough of a respectively neighboring deformed structural ring, then the crest of the one ring can be connected, via a connecting member, with the trough of the respectively neighboring ring by which a very high flexibility of the total mesh structure and, associated therewith, an increased capacity for growth of the supporting prosthesis can be achieved.

According to a further embodiment, it is possible to connect a crest of one structural ring with a middle point, i.e. with a point on or next to the middle line M as defined above of the respectively neighboring structural ring. According to a further embodiment it is possible to connect a middle point, i.e. a point on or next to the middle line M of one structural ring with the middle point of the respectively neighboring structural ring. According to a further embodiment, it is possible to connect a trough of one structural ring with a middle point, i.e. with a point on or next to the middle line M of the respectively neighboring structural ring.

According to a further embodiment of the present invention, the connecting members can be designed as rings, clamps or, extending in parallel to the main axis of the supporting prosthesis (also called "longitudinal axis of the supporting prosthesis"), loops, threads, wires or struts.

Here, the connecting members can be connected with the respectively neighboring structural rings in a loose or rigid fashion. By attaching in a loose fashion, for example, by polymers or metals which are softer than the basis material of the supporting prosthesis, one can achieve a very high flexibility of the total mesh structure. Such a loose connection of the structural rings can also be effected by wire, a clip or suture material. Predetermined breaking points can also be provided on connecting members.

In contrast, a solid attachment of the connecting members with their respectively structural rings has a stiffening effect on the mesh structure. It is preferred that the connecting members which connect to respectively neighboring structural rings are fashioned as solid struts, which are preferably seamlessly integrated into the structure of the respectively neighboring structural rings. In the event that the supporting prosthesis capable of growth is to be cut out of a tube blank, for example by means of a laser, such solid struts or bridges can easily be made in a manner known to the skilled person in that in the positions where connecting members are to be later provided, the blank is not cut.

It is however also conceivable that in one segment of the supporting prosthesis, loose connecting members are used, whereas in another segment of the supporting prosthesis, solid connecting members are used. A mixture of loose and solid connecting members over the entire structure of the mesh structure is also conceivable.

According to a further embodiment of the present invention, the structural rings and/or the connecting members are composed at least in part of a biologically degradable material, for example, a biologically degradable metal, such as for example a stainless steel or biologically degradable polymer.

If the structural rings and/or the connecting members are composed only in part of a biologically degradable material, this material dissolves over the course of time following implantation in vivo, so that only the parts of the structural rings and/or connecting members which are not composed of non-degradable material persist. In this way, the desired supporting function of the supporting prosthesis is assumed in the long term by the remaining, non-degradable parts of the structural rings and/or connecting members in interaction with the cell tissue which has developed in the interim. If the structural rings and/or connecting members are composed completely of biologically degradable material, the total material of the mesh structure disappears with time, so that only the interim-generated cell tissue of the cells which initially populated the supporting prosthesis assumes the desired support function. For some patients, such a support function can be entirely adequate. The choice of the materials, i.e. whether the supporting prosthesis according to the invention is composed completely, partially or not at all of biologically degradable material, is dependent as a rule on the patient to be treated. In general though, it can be said that an increased need of support function will make designs with higher proportions of non-biologically degradable material preferable, as such supporting prostheses according to the invention are capable of exerting a high radial supporting force even after growth, i.e. after the mesh structure has been at least partially forced apart at its predetermined breaking points.

According to a further embodiment of the invention, at least a part of the structural rings as well as the connecting members of the supporting prosthesis is composed of a polymer. Here, the entire supporting prosthesis can be composed of the same polymer, or the structural rings as well as the connecting members can be composed of one polymer and the predetermined breaking points can be composed of another polymer. In this way, for example, the structural rings and the connecting members can be composed of one non- or only poorly biologically degradable polymer, whereas the predetermined breaking points can be composed of one or more biologically degradable polymers. By such a design, the growth characteristics can be controlled, as described in further detail below.

According to a further embodiment of the invention, such a supporting prosthesis made of polymers comprises, on its inner side, a heart valve, for example a heart valve prepared by means of tissue engineering with autologous tissue or a tissue engineered vessel. In addition to the greatly reduced risk of an immune rejection, such heart valves prepared by means of tissue engineering are also excellently suitable for use in a supporting prosthesis capable of growth since, by their nature, they can grow.

According to a further embodiment, the supporting prosthesis capable of growth can be a heart valve-carrying supporting prosthesis. Here, the heart valve and/or the supporting prosthesis itself can include tissue engineered autologous or heterologous tissue or tissue foreign to the body, decellularized or fixed heart valve tissue. In the ideal case, both the supporting prosthesis according to the invention as well as the possibly present heart valve includes the same type of tissue, which is preferably autologous tissue. Such a heart valve can grow with the supporting prosthesis.

Polymers which can be considered suitable as non- or only poorly biologically degradable polymers are primarily PTFE, Dacron, PHA and poly-3-hydroxybutyrate P3HB.

Independently of which material the supporting prosthesis is composed of, the supporting prosthesis as described above can preferably be populated with cells native to the body, the supporting prosthesis populated in this way is folded or "crimped" into the size or diameter required for implantation, and the thus compressed supporting prosthesis is for example introduced via a vessel catheter into the desired location in the body. In this way, the supporting prosthesis can exert its support function in the vessel following possible necessary expanding by means of a balloon catheter. This applies both for supporting prostheses with, as well as without, heart valves.

According to a further embodiment of the present invention, the biologically degradable material is chosen from at least one alloy, at least one stainless steel and/or at least one polymer with shape memory. Suitable alloys with shape memory are for example primarily nickel-titanium alloys, such as for example the known nitinol, or aluminium alloys, magnesium alloys or iron alloys. Suitable polymers with shape memory are for example tert-butylacrylate or poly(ethylenglycol)dimethacrylate or PCL combined with 2,4-toluenediisocyanate ethylenglycol.

Suitable biologically degradable polymers are primarily polyglycolic acid (PGA), polylactic acid (PLA), polyhydroxalkanoate (PHA) and poly-4-hydroxybutyrate (P4HB), poly-caprolactones (PLGA), polycarbonates, polyamides, polyanhydrides, polyamino acids, polyorthoesters, polyacetates, polycyanoacrylates as well as degradable polyurethanes and non-erodible polymers such as polyacrylates, ethyleneviny-lacetate polymers and other substituted cellulose acetates as well as derivatives thereof. Polyesters are preferred. Preferred biologically degradable polymers include polymers of the following groups: polyesters of the hydroxycarboxy acids, polyanhydrides of the dicarboxyesters and copolymers of the hydroxycarboxy acids and of the dicarboxyesters.

In a further embodiment, the material is composed of a synthetic polymer of at least one of the following monomers: glycolide, lactide, p-dioxanone, caprolactone, trimethylenecarbonate, butyrolactone. In particular embodiments, the material is chosen from a group consisting of polymers or copolymers of glycolic acid, lactic acid and sebacic acid. Polyglycolic acid polymers are preferred.

These polymers can be used both pure as well as in mixtures of two or more of the named substances or mixtures of these substances with further biologically degradable polymers. In a preferred embodiment, a mixture of 80-98% PGA and 20-2% PHA is used.

In a further special embodiment, the biologically degradable material includes polyhydroxyalkanoate (PHA). Here, PHA can be coated with a further non-degradable polymer or can itself serve as a coating. A preferred polyhydroxyalkanoate for this use is degraded in vivo within less than 9 months, more preferred within less than 6 months and most preferred within less than 3 months. A preferred composition of the polyhydroxyalkanoate contains 2-, 3-, 4- or 5-hydroxy acids, e.g. poly-4-hydroxybutyrates. Further, the composition can contain a poly-4-hydroxybutyrate-co-3-hydroxybutyrate as well as combinations thereof. Poly-4-hydroxybutyrate is most preferred.

In a further special embodiment, the biologically degradable material includes homopolymers and copolymers with any desired combination of the following monomers: 3-hydroxybutyrate, 3-hydroxyvalerate, 3-hydroxyproprionate, 2-hydroxybutyrate, 4-hydroxybutyrate, 4-hydroxyvalerate, 3-hydroxyhexanoate, 3-hydroxyheptanoate, 3-hydroxyoctanoate, 3-hydroxynonanoate, 3-hydroxytridecanoate, 3-hydroxytetradecanoate, 3-hydroxapentadecanoate, 3-hydroxyhexadecanoate 3-hydroxyheptadecanoate and 3-hydroxyoctadecanoate.

According to a further embodiment of the invention, the supporting prosthesis can be made of a non-biologically degradable material and can be coated with one or more biologically degradable materials, e.g. polymers. It is further possible according to a further embodiment of the invention that the supporting prosthesis is made of a biologically degradable material and is coated with one or more non-biologically degradable materials. Both the biologically degradable material as well as the non-biologically degradable material can be a polymer or a metal.

According to a further embodiment of the present invention, the at least one predetermined breaking point is disposed on or next to the middle point between a crest and a trough of the periodically deformed structural ring, i.e. on or next to the intersection point of the structural ring with the middle line M as defined above. However, the at least one predetermined breaking point can also, additionally or alternatively, be disposed on the crests and/or troughs of the periodic deformations of the structural ring.

As the supporting prosthesis according to the invention grows, radial forces directed from inside to outside are exerted on the mesh structure of the supporting prosthesis. If the supporting prosthesis is stretched open during the growth process, these forces are concentrated at the crests and troughs of the structural rings, since these crests and troughs of the supporting prosthesis in total confer a large part of its flexional capacity. If the predetermined breaking points are disposed exclusively on the crests and troughs of the periodically deformable structural ring, the danger exists that the total mesh structure will be prematurely broken apart, in which case it is possible that a large part of its support function would be disadvantageously lost. However, if the predetermined breaking points are exclusively or predominately disposed on or next to the middle point between the crests and troughs of the periodically deformable structural ring, the breaking apart of the mesh structure can in some cases be delayed.

By a targeted mixture of the positions at which the predetermined breaking points are disposed, one can control the breaking tendency of the supporting prosthesis in a very advantageous manner. The more predetermined breaking points are disposed at crests and/or troughs of a periodically deformable structural ring, the greater is the tendency to break. The more predetermined breaking points are disposed on or next to the middle points of a periodically deformable structural ring, the lower is the tendency to break.

The concrete design of the predetermined breaking points is not restricted, as long as they can exert their function as described above. Concretely, this function can be realized in different manners. In a supporting prosthesis made from a metallic material, a predetermined breaking point can for example be designed as at least a perforation in a strut of a structural ring or in a connecting member. Such perforations can be of different types, for example, as one or more piercing holes and/or one or more non-piercing cavities in the material of the supporting prosthesis. The shape of the holes or the cavities is not restricted: it can be round, elliptical, polygonal, rectangular and/or square. The cavity can also be designed as a notch or multiple notches in the material of the supporting prosthesis, said notches for example running perpendicularly or diagonally over the width of a strut of a structural ring and/or of a connecting member. It is also possible to arrange such notches or narrowings on both sides of a strut of a structural ring and/or of a connecting member such that two notches define the same predetermined breaking point from both sides of the structural ring or both sides of the connecting member (i.e. from above and below), i.e. on the sides of the supporting prosthesis both facing the vessel wall as well as the wall of the vessel lumen.

Alternatively or supplementary thereto, one or two notches may be disposed to the right and the left at the same position, i.e. in the same height of the strut as the two notches disposed above and below. In this way, the strength of a predetermined breaking point can be adjusted by creating it out of one, two, three or four notches which are all disposed at the same height of the strut or of the connecting member. Although these embodiments assume a strut and/or a connecting member with a four-sided cross-section, it should be noted that corresponding considerations apply for struts and/or connecting members with differently designed cross-sections.

It is also possible to design a predetermined breaking point such that it breaks apart upon exceeding, at a point or along a line, the plastic deformability of a strut of the structural ring and/or to create a predetermined breaking point by providing point-wise or linear differences in the structural density of the supporting prosthesis material. Predetermined breaking points can also be fashioned by effecting point-wise or linear damage to the surface structure or to the inner structure of the structural ring and/or of the connecting member (for example, by a local increase of the porosity of the material, for example by incorporation of nano-particles in the region of the predetermined breaking point). Positionally restricted or unrestricted mixture of the basis material of the supporting prosthesis with polymer and/or with polymer interponates, wires, threads and/or organic interponates such as for example collagen is also conceivable.

A predetermined breaking point can also be designed as a cut or a gap in the material of the supporting prosthesis (i.e. in the structural ring or in the connecting member). This cut or gap can be covered with a non-metallic material, for example a biologically degradable material in the region of the predetermined breaking point, so that at first only the biologically degradable material holds the predetermined breaking point together. This can for example be effected in that the biologically degradable material overlaps both sides of the cut or the gap on the material of the structural ring or of the connecting member and is connected with this. When the biologically degradable material dissolves with time in the body, its support function is correspondingly reduced until either the breaking forces developing due to the growth exceed the support capacity of the biologically degradable material, or the biologically degradable material completely dissolves and exposes the underlying cut or gap, so that the supporting prosthesis can grow unhindered (or can at least be stretched open by means of balloon angioplasty). By suitable choice of the biologically degradable material used at the predetermined breaking point, the speed of the growth process can be controlled, as it is known that different biologically degradable materials dissolve in vivo at different rates.

As mentioned above, the at least one predetermined breaking point can be designed such that it can be forced open, dissolved, weakened or stretched by external influence. The external influence can be chosen from sound waves, at least one magnetic field, a combination of a magnetic field and an electromagnetic field; electromagnetic radiation, electrical energy and any desired combination thereof. The external influence can be applied from inside or outside the body; it proceeds at least from outside the supporting prosthesis. If the external influence is applied from inside the body, it can, for example, be applied with the help of an intravascular catheter or in a minimally invasive manner with the help of endoscopy. The sound waves can for example be ultrasound and/or shock waves. The combination of magnetic field and electromagnetic field can, for example, be nuclear magnetic resonance imaging (MRI). The electromagnetic radiation can, for example, be X-ray radiation or infrared radiation (thermal energy). For example, a local increase in temperature can achieve a steep decrease in the stiffness of a predetermined breaking point (stretching of the predetermined breaking point by plastic deformation) or even a break in the predetermined breaking point.

According to a further embodiment of the invention, the predetermined breaking point can be designed such that its rigidity or holding capacity only decreases beyond a strain of predetermined duration or of predetermined strength. For example, the predetermined breaking point of a supporting prosthesis capable of growth and intended for the aorta region can be fashioned such that the threshold value of the maximally tolerated mechanical strain of the predetermined breaking point material caused by the pumping of the heart is only reached after a certain number of heartbeats. Assuming an average heart rate, one can effectively preprogram the duration following implantation after which the supporting prosthesis begins to dissolve or to stretch. This enables a control of the supporting prosthesis' growth rate which is particularly advantageous in the use in small children, since in this way, the number of surgical procedures can be significantly reduced. It is of course also imaginable that the strain to which the predetermined breaking point is to be subjected is of a non-mechanical nature.

Since the amount of the biologically degradable material at the predetermined breaking points is as a rule very small, one need not fear inflammatory reactions upon its dissolution, as is the case in the prior art when supporting prostheses composed completely of biologically degradable material dissolve.

A corresponding design using a biologically degradable material is also possible in the case when, instead of a cut or a gap, a perforation and/or a notch are present in the material of the supporting prosthesis.

It is also possible, independent of the design as perforation, notch, cavity, gap or cut, to apply multiple layers of different biologically degradable materials to the at least one predetermined breaking point, to enable the supporting prosthesis to break apart in a chronologically graduated manner. In this way, it can for example be ensured that the dissolution of the predetermined breaking point proceeds very slowly, and only after a longer amount of time (i.e. after the slowly dissolving outer layer has disappeared) the rate of dissolution of the predetermined breaking point and the growth potential of the supporting prosthesis associated therewith increases, or vice versa.

It is also possible that a supporting prosthesis comprises a combination of predetermined breaking points of different design. For example, a supporting prosthesis may comprise one or more predetermined breaking points as perforations without biologically degradable material and one or more predetermined breaking points as cuts and/or gaps coated with one or more biologically degradable materials. In this way, it can be ensured that different regions of the same supporting prosthesis grow at different rates in vivo within the same amount of time. The supporting prosthesis according to the invention thus allows a very high degree of flexibility in the adaptation to the most diverse physiological requirements.

It is also possible to use non-biologically degradable polymers in the region of the predetermined breaking points. The predetermined breaking point can be designed as described above, i.e. as a perforation, groove, cavity, gap or cut. If for example non-biologically degradable polymer is applied to both sides overlapping a cut or a gap in the structural ring and/or in the connecting member, then the strength of the predetermined breaking point, and thus also the growth capacity of the supporting prosthesis, depends on the strength of the non-biologically degradable polymer. In this way, given a known material strength of the non-biologically degradable polymer, the strength or the growth characteristics of the supporting prosthesis may be controlled as dictated by physiological requirements.

According to a preferred embodiment, the predetermined breaking points thus comprise a non-metallic material, for example a polymer material. This material can be a polymer, and can be biologically degradable or non-biologically degradable. In addition to the advantages set out above, such a design implies certain additional advantages.

First, as a rule, polymer materials have a lower tensile strength than metallic materials, said tensile strength directly depending, as implied above, on the degree of degradation of the material used. In the supporting prosthesis capable of growth according to the invention, an increased tensile strength has a growth-inhibiting effect on the predetermined breaking points, since the predetermined breaking points can be ripped apart only with difficulty. Conversely, by choosing a material with increased ripping tendency at the predetermined breaking points, the growth ability of the supporting prosthesis according to the invention can be promoted. In this way, one has the possibility by using a non-metallic material of a known tensile strength at the predetermined breaking points to provide supporting prostheses with different growth abilities. Thus, the growth ability of the provided supporting prosthesis can be adapted to the specific clinical requirements of any patient.

Second, designing the predetermined breaking points with non-metallic material ensures that, after the breaking apart of the mesh structure due to the growth or due to expansion, no sharp-edged corners of metal are formed which could later injure the supported vessel wall or even break off and disrupt a distant location in the vessel system.

For the case that the mesh structure of the supporting prosthesis is composed of a metallic material and the predetermined breaking points consist of or include a non-metallic material, it is preferred that the non-metallic material in the region of the predetermined breaking points is applied to the metallic material of the supporting prosthesis by coating. Here, the metallic material of the mesh structure preferably comprises, at least in the region of the predetermined breaking points, i.e. below the coating of non-metallic material, a polished surface structure or a rounded shape. In this way, it is ensured that, even following the breaking open of the predetermined breaking points and, as the case may be, following the dissolution of the non-metallic material, a smooth surface of the mesh structure or no sharp edge on these predetermined breaking points remains, by which the mentioned advantage of the reduced risk of injury is realized. Methods for polishing metallic fine structures, such as for example, electro-polishing are known to the skilled person.

According to a further embodiment of the present invention, a mesh structure comprises at each of the two terminal regions of the supporting prosthesis, relative to the longitudinal axis of the supporting prosthesis, at least two structural rings, wherein the two respective structural rings disposed closest to the middle point of the longitudinal axis of the supporting prosthesis are connected with one another via elongated connecting members. In this way, a supporting prosthesis is formed which comprises two respective terminally disposed mesh structure parts as well as a middle part which connects the two terminally disposed mesh structures with one another, via preferably elongated connecting members. Such a supporting prosthesis is advantageous in cases where a branching vessel is to be supported in the long term. The supporting prosthesis according to this embodiment can be inserted into the vessel to be supported in such a way that the one terminal mesh structure is disposed above the branching point and the other terminal mesh structure is disposed below the branching point, while the elongated connecting members are located in the middle region of the supporting prosthesis are located at the height of the branching point. In this way, damaging or occluding the branching point is avoided, since the elongated middle portion of the supporting prosthesis is less robust and thus exerts a lower radial force on the vessel walls than the terminally disposed mesh structures. In this way, the sensitive point of the vessel is advantageously spared. In addition, the larger lumen of the mesh openings allows an unhindered flow of blood into the branching vessel. Over the course of time, both of the terminal mesh structures can grow as set out above, whereby a long-term supporting function of the regions of the vessel above and below the sensitive point of the vessel is ensured. According to a further embodiment of the present invention, the length of the elongated connecting members is 0.75 to 3-fold of the amplitude A of the deformations of the structural rings mentioned above. It is preferred that the length of the elongated connecting members is 1 to 2-fold of the amplitude A mentioned above. According to this embodiment, each terminal mesh structure comprises 2-8, preferably 2-6, especially preferably 1-4, but preferably not more than 10 structural rings.

The proximal and distal supporting regions (that is, the proximal and distal mesh structures) can be designed to be harder and stiffer than the elongated connecting members disposed therebetween. They can also be provided with anchoring structures in order to prevent slipping within the vessel due to the blood flow.

According to a further embodiment of the present invention, the supporting prosthesis comprises a heart valve on its inner side. The heart valve can be sewed, glued, clamped or woven to the supporting prosthesis, wherein it is preferred to sew the heart valve to the supporting prosthesis. Here, it can be advantageous to produce the heart valve by means of a tissue engineering method. In this tissue engineering method, it can be especially advantageous to use cells of the same origin as used to populate the mesh structure of the supporting prosthesis, that is homologous or autologous cells. It can thus be ensured that the respective growth rates of, on the one hand, the heart valve located on the inside of the supporting prosthesis and, on the other hand, the mesh structure of the supporting prosthesis, remain the same during the entire growth process.

EXAMPLES

The following example explains in a non-limiting manner how a supporting prosthesis capable of growth can be prepared.

Example 1

Manufacture of a Supporting Prosthesis Capable of Growth

Figure 1:
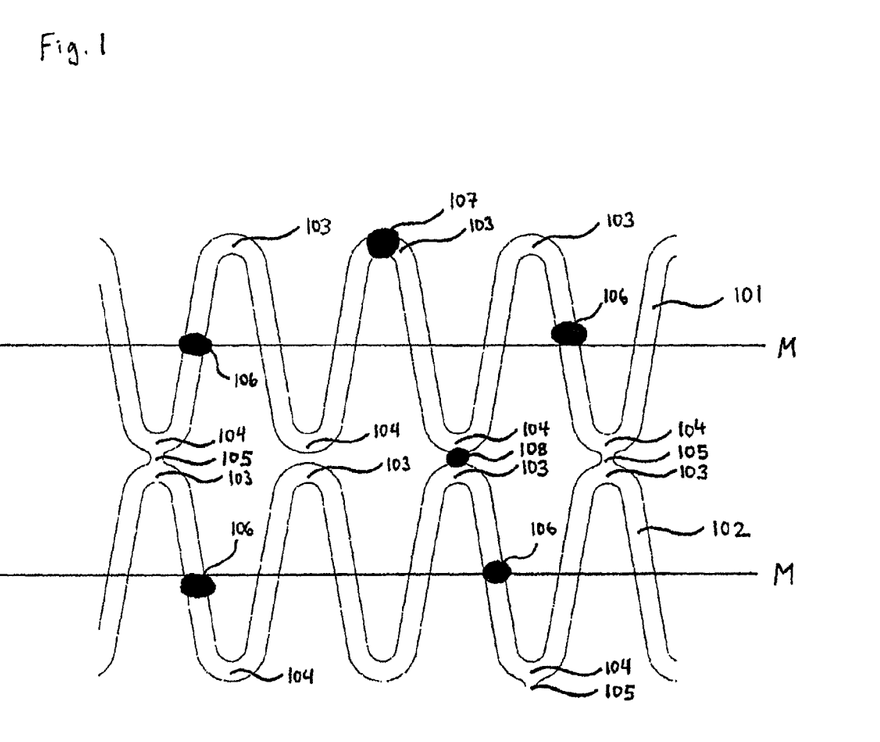
Figure 2:
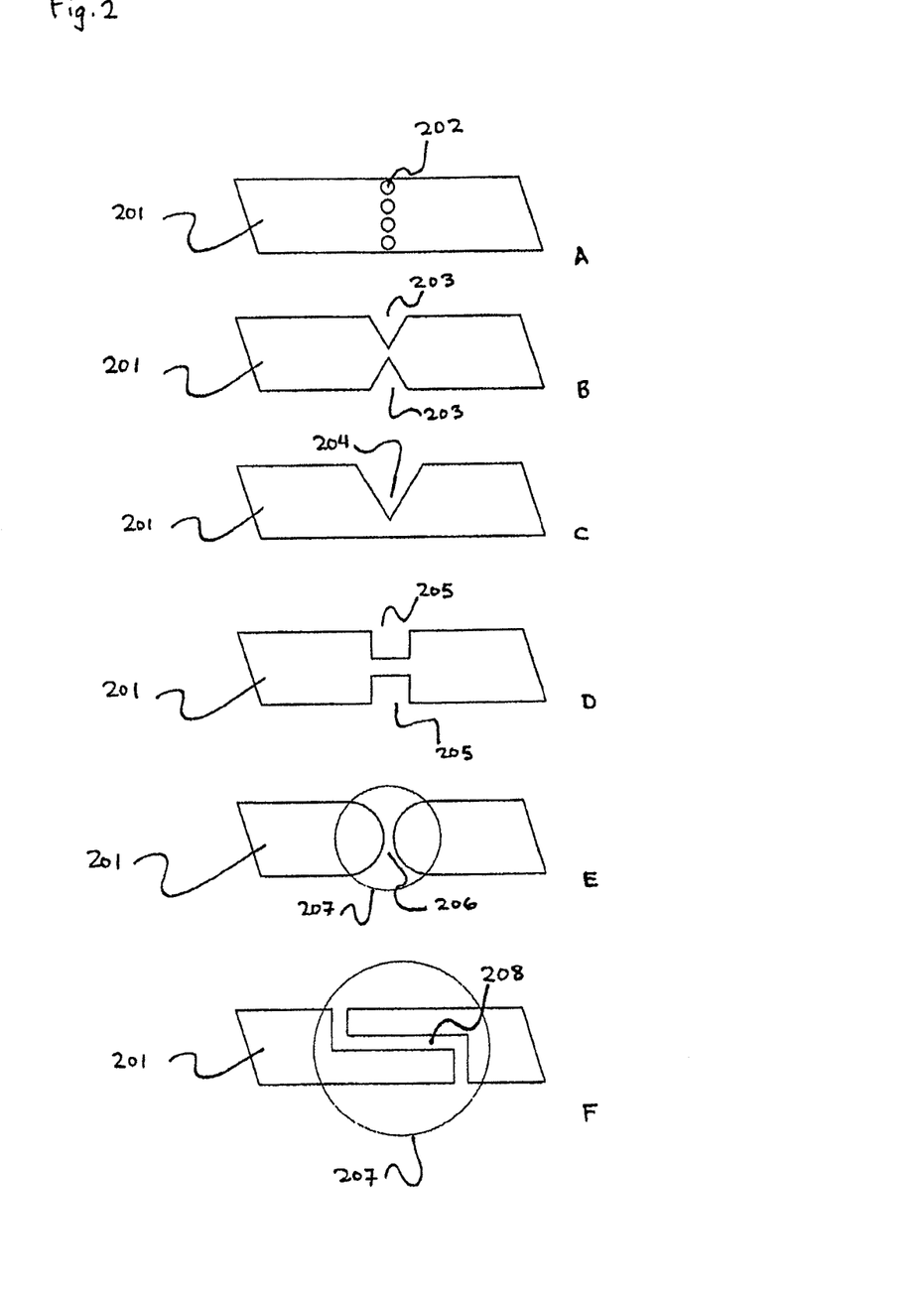
FIG. 2A: A segment (201) of a structural ring or of a connecting member with a predetermined breaking point which is designed as a perforation (202).
FIG. 2B A segment (201) of a structural ring or of a connecting member with a predetermined breaking point which is designed with triangular-shaped notches (203) disposed above and below.
FIG. 2C: A segment (201) of a structural ring or of a connecting member with a predetermined breaking point which is designed with a triangular-shaped notch (204) disposed above.
FIG. 2D: A segment (201) of a structural ring or of a connecting member with a predetermined breaking point which is designed with rectangular-shaped notches (205) above and below.
FIG. 2E: A segment (201) of a structural ring or of a connecting member with a predetermined breaking point which is designed with a rounded cut and is coated with a polymer (207)
FIG. 2F: A segment (201) of a structural ring or of a connecting member with a predetermined breaking point which is designed with a step cut (208) and is coated with a polymer (207).
FIG. 2G: A cross-section (211) of a structural ring or of a connecting member with a predetermined breaking point which is designed with rectangular notches (205) disposed above and below.
FIG. 2H: A cross-section (211) of a structural ring or of a connecting member with a predetermined breaking point which is designed with rectangular-shaped notches (205) disposed above, below, right and left.
Figure 3:
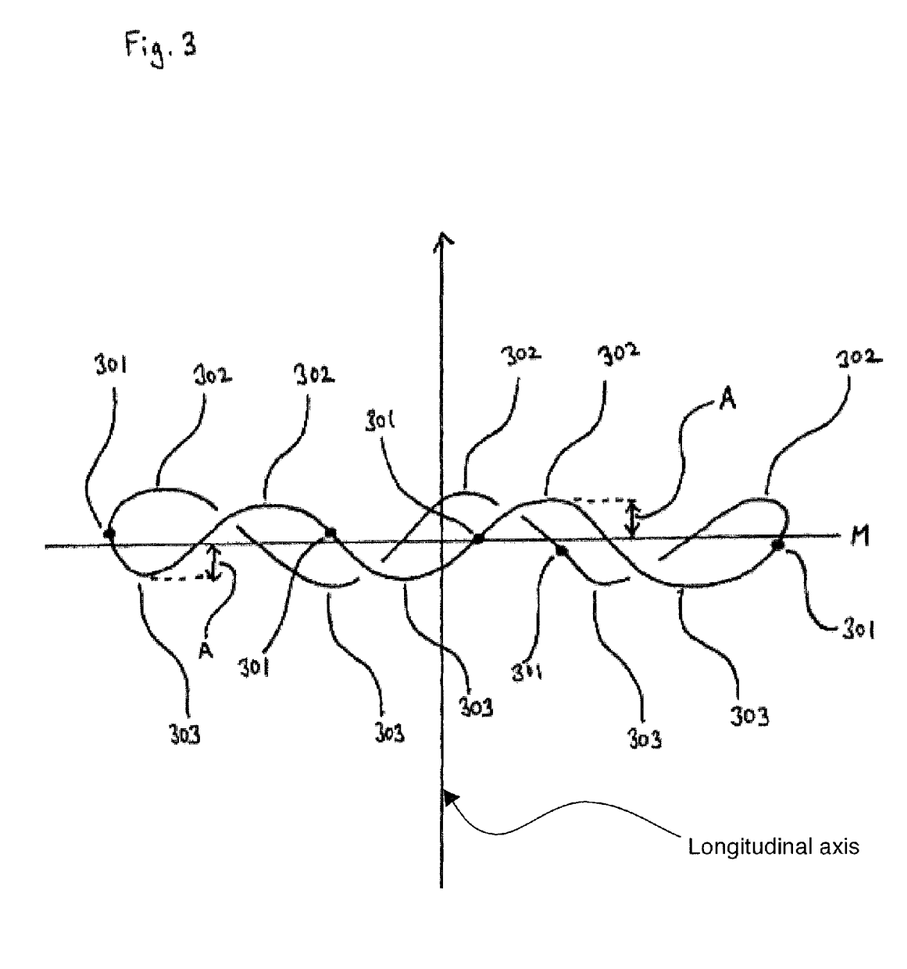
FIG. 3: A perspective view of a structural ring with sinusoidal deformations. The structural ring shown comprises 5 crests (302), 5 troughs (303) and 5 predetermined breaking points (301) on or next to the middle line M extending perpendicular to the longitudinal axis of the supporting prosthesis. Also shown is the amplitude A. Not shown are connecting members which connect the depicted structural ring with a neighboring structural ring in the mesh structure.

In general, the production of a supporting prosthesis capable of growth includes the following method steps:
1. Cutting with a laser
2. Electro-polishing
3. Checking/cleaning 1.1 Cutting with a Laser The supporting prosthesis is manufactured from highly precise material (e.g. 316L, L605, or nitinol) using a solid state laser. In order to freely design the supporting prosthesis, one strives for a method which allows user-defined cutting guidance on a tube. A laser fulfils these requirements in conjunction with a coordinate table, a round axis and a specially manufactured tube guider which precisely guides the tube in the required degrees of freedom under the laser cutting head. The supporting prosthesis structure and the predetermined breaking points, which are in this case mechanical (as for example depicted in FIG. 2) are cut into the tube in a one-step process. After removing the "windows", i.e. the regions which have been cut out, the struts of the supporting prosthesis and thus the finished supporting prosthesis structure remains. This includes not only the structural rings, but also the connecting members connecting these.

1.2 Electro-Polishing

Electro-polishing, generally known to the skilled person, is used to round-off the edges of the supporting prosthesis resulting from the laser cutting in order to minimize damage to the vessel and implantation balloon and to smooth the surface of the supporting prosthesis. An electrochemical polishing method adapted to the special requirements of supporting prosthesis production is used. The adaptation for the processing of supporting prostheses mainly includes a polishing apparatus which ensures a uniform current flow during the polishing process. During this, the supporting prostheses are continually moved in the electro-polishing bath and are simultaneously put under voltage.

1.3 Checking/Cleaning

After the polishing by the electro-polishing method described above, the supporting prosthesis are cleaned of polishing residues by etching and multiple rinses and are optically checked as well as measured and packaged. In the optical check, the entire surface is assessed. Here, supporting prostheses which i.a. do not fulfil the following criteria, are rejected:
uniform, smooth surface
continuous rounding of edges without points.

The invention claimed is:

1. A tubular supporting prosthesis, comprising:
a mesh structure,
wherein the mesh structure comprises at least two structural rings which are connected to each other via connecting members and are disposed point-symmetrically about the longitudinal axis of the supporting prosthesis,
wherein the structural rings comprise at least one predetermined breaking point,
wherein said prosthesis is capable of growth, and
wherein the at least one predetermined breaking point comprises multiple layers of different biologically degradable materials, wherein the multiple layers of different biologically degradable materials are located only at the predetermined breaking point area, such that the rate of dissolution of the predetermined breaking point proceeds in a chronologically graduated manner.

2. The supporting prosthesis according to claim 1, wherein at least one structural ring of the mesh structure comprises n periodic deformations extending along the longitudinal axis of the supporting prosthesis and forming crests and troughs, said deformations comprising an amplitude A relative to the longitudinal axis of the supporting prosthesis, wherein n=16-70.

3. The supporting prosthesis according to claim 2, wherein the deformations are sinusoidal, rectangular, saw-tooth or triangular in shape.

4. The supporting prosthesis according to claim 2, wherein the number of the periodic deformations of two respectively neighboring structural rings is identical or differs from each other by a whole number.

5. The supporting prosthesis according to claim 2, wherein two neighboring structural rings are phase-shifted with respect to one another such that crests of one structural ring are connected with troughs of a respectively neighboring structural ring via the connecting members.

6. The supporting prosthesis according to claim 1, wherein the connecting members are fashioned as rings, clamps or loops, threads, wires or struts, said loops, threads, wires or struts extending parallel to the longitudinal axis of the supporting prosthesis.

7. The supporting prosthesis according to claim 1, wherein the structural rings and/or the connecting members are made at least in part of a biologically degradable material.

8. The supporting prosthesis according to claim 7, wherein the biologically degradable material is chosen from at least one alloy, at least one polymer or at least one stainless steel with shape memory.

9. The supporting prosthesis according to claim 8, wherein the alloy with shape memory is a nickel-titanium alloy, an aluminium alloy, a magnesium alloy or an iron alloy.

10. The supporting prosthesis according to claim 7, wherein the biologically degradable material is a polymer selected from the following group: polyglycolic acid (PGA), polylactic acid (PLA), polyhydroxyalkanoate (PHA), poly-4-hydroxybutyrate (P4HB), polycaprolactones (PLGA), polycarbonates, polyamides, polyanhydrides, polyamino acids, polyorthoesters, polyacetates, polycyanoacrylates as well as degradable polyurethanes and non-erodible polymers such as polyacrylates, ethylenevinylacetate polymers, other substituted cellulose acetates as well as derivatives thereof, polyesters of the hydroxycarboxy acids, polyanhydrides of the dicarboxyesters, copolymers of the hydroxycarboxy acids and of the dicarboxyesters, a synthetic polymer of at least one glycolide, lactide, p-dioxanone, caprolactone, trimethylenecarbonate and/or butyrolactone, polymers or copolymers of glycolic acid, lactic acid and sebacic acid, polyhydroxyalkanoate compositions of 2-, 3-, 4- or 5-hydroxy acids, e.g. poly-4-hydroxybutyrates, a poly-4-hydroxybutyrate-co-3-hydroxbutyrate, homopolymers and copolymers with any desired combination of 3-hydroxybutyrates, 3-hydroxyvalerate, 3-hydroxyproprionate, 2-hydroxbutyrate, 4-hydroxybutyrate, 4-hydroxyvalerate, 3-hydroxyhexanoate, 3-hydroxyheptanoate, 3-hydroxyoctanoate, 3-hydroxynonanoate, 3-hydroxytridecanoate, 3-hydroxytetradecanoate, 3-hydroxypentadecanoate, 3-hydroxyhexadecanoate, 3-hydroxyheptadecanoate and 3-hydroxyoctadecanoate or a combination thereof.

11. The supporting prosthesis according to claim 2, wherein the at least one predetermined breaking point is disposed on or next to a middle line between neighboring crests and troughs of the periodic deformations of the structural ring.

12. The supporting prosthesis according to claim 1, comprising a mesh structure at each of two terminal ends of the supporting prosthesis relative to a longitudinal axis of the supporting prosthesis, wherein of the at least two structural rings, two structural rings disposed closest to a middle point of the longitudinal axis of the supporting prosthesis are connected with one another via elongated connecting members.

13. The supporting prosthesis according to claim 2,
wherein the mesh structure of two terminal ends of the supporting prosthesis relative to a longitudinal axis of the supporting prosthesis,
wherein of the at least two structural rings disposed closest to a middle point of the longitudinal axis of the supporting prosthesis are connected with one another via elongated connecting members,
wherein the length of the elongated connecting members is 0.75-3-fold of the amplitude A.

14. The supporting prosthesis according to claim 1, further comprising, on an inner side thereof, a heart valve or a vessel.

15. The supporting prosthesis according to claim 14, wherein the heart valve is sewed, glued, clamped or woven to the supporting prosthesis.

16. The supporting prosthesis according to claim 14, wherein the heart valve is the product of a tissue engineering method.

17. The supporting prosthesis according to claim 1, wherein the at least one predetermined breaking point is made of a non-metallic material.

18. The supporting prosthesis according to claim 1, wherein the at least one predetermined breaking point is formed such that it can be broken apart, dissolved or weakened by external influence.

19. The supporting prosthesis according to claim 18, wherein the external influence is chosen from: sound waves; at least one magnetic field; a combination of magnetic field and electromagnetic field; electromagnetic radiation; electrical energy and any desired combination thereof.

20. The supporting prosthesis according to claim 19, wherein the sound waves are ultrasound and/or shock waves.

21. The supporting prosthesis according to claim 19, wherein the combination of magnetic field and electro-magnetic field is magnetic resonance imaging (MRI).

22. The supporting prosthesis according to claim 19, wherein the electromagnetic radiation is X-ray radiation or infrared radiation (thermal energy).

23. The supporting prosthesis according to claim 18, wherein external influence is applied from inside or outside of the body.

24. The supporting prosthesis according to claim 23, wherein the influence from within the body in applied with the help of an intravascular catheter or in a minimally invasive manner with the help of endoscopy.

25. The supporting prosthesis according to claim 8, wherein the polymer with shape memory is chosen from tert-butylacrylate, poly(ethyleneglycol)dimethacrylate or PCL combined with 2,4-toluenediisocyanate ethyleneglycol.

26. The supporting prosthesis according to claim 1, wherein the connecting members comprise at least one predetermined breaking point.

27. The supporting prosthesis according to claim 2, wherein n=20-56.

28. The supporting prosthesis according to claim 2, wherein n=24-42.

29. The supporting prosthesis according to claim 13, wherein the length of the elongated connecting members is 1-2 fold of the amplitude A.

30. A tubular supporting prosthesis, comprising:
a mesh structure,
wherein the mesh structure comprises at least two structural rings which are connected to each other via connecting members and are disposed point-symmetrically about the longitudinal axis of the supporting prosthesis,
wherein the structural rings comprise at least one predetermined breaking point,
wherein said prosthesis is capable of growth, and
wherein the at least one predetermined breaking point comprises multiple layers of different biologically degradable materials, wherein at least one of the multiple layers of different biologically degradable materials, the multiple layers of different biologically degradable materials being located only at the predetermined breaking point, has a different rate of dissolution than one or more of the other multiple layers at the predetermined breaking point, such that the rate of dissolution of the predetermined breaking point proceeds in a chronologically graduated manner.

31. A tubular supporting prosthesis according to claim 1 or claim 30, wherein the prosthesis is coated with one or more biologically degradable materials, or one or more non-biologically degradable materials.

* * * * *